(12) United States Patent
Yanagimachi et al.

(10) Patent No.: US 6,593,139 B1
(45) Date of Patent: Jul. 15, 2003

(54) INITIATION OF FULL MAMMALIAN OOCYTE ACTIVATION BY MULTIPLE SPERM COMPONENTS

(75) Inventors: Ryuzo Yanagimachi, Honolulu, HI (US); Anthony C. F. Perry, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/478,848

(22) Filed: Jan. 7, 2000

(Under 37 CFR 1.47)

Related U.S. Application Data

(60) Provisional application No. 60/115,118, filed on Jan. 8, 1999.

(51) Int. Cl.$^7$ .............................. C12N 5/00; C12N 5/02; C12N 15/00; A01K 67/00; A01K 67/033

(52) U.S. Cl. ........................... 435/375; 435/325; 800/8; 800/21

(58) Field of Search .................... 800/8, 21; 424/184.1; 435/325, 375

(56) References Cited

PUBLICATIONS

Sasgawa, I. et al. Comparison of methods for activating mouse oocytes for spermatid nucleus transfer. *Zygote* 4, 269–274 (1996).
Swann, K. et al. On the search for the sperm oscillogen. *Mol. Hum. Reprod.* 4, 1010–1012 (1998).
Perry, A. C. et al. Mammalian oocyte activation by the synergistic action of discrete sperm head components: induction of calcium transients and involvemetn of proteolysis. *Developmental Biology* 217, 386–393 (2000).
Yanagimachi, R. Intracytoplasmic sperm injection experiments using the mouse as a model. *Human Reproduciton* 13, Supplement 1, pp. 87–98, 1998.
Ohsumi, K. et al. (1986). Development of pronuclei from human spermatozoa injected microsurgically into frog (Xenopus) eggs. *J. Exp. Zoology* 237: 319–325.
Almedida, E. A. C. et al. Mouse egg integrin $\alpha_6\beta_1$ functions as a sperm receptor.*Cell* 81:1095–1104 (1995).
Arnoult, C. Activation of mouse sperm T–type $Ca^{2+}$channels by adhesion to the egg zona pellucida. *Proc Natl. Acad. Sci. USA* 93: 13004–13009 (1996).
Bellé, A. R. & O'Brien, D. A. Mechanism and Control of Animal Fertilization. Academic Press: New York: 5–137 (1983).
Berridge, M. J. Inositol triposphate and calcium signalling. *Nature* 361: 315–325 (1993).
Brown, D.& Rothery, P. Models in Biology: Mathematics, Statistics, and Computing. Clarendon Press: Oxford: 130–135 (1993).

Calvin, H. I. et al. Estimation and manipulation of glutahione levels in prepubertal mouse ovaries and ova: relevance to sperm nucleus transformation in the fertilized egg. *Ganete Res* 14: 265–275 (1986).
Carroll, D. J. et al. Calcium release at Fertilization in starfish eggs is mediated by phospholipase $C_\gamma$. *J. Cell Biol.* 138: 1303–1311 (1997).
Cheek, T. R. et al. Fertilization and thimerosal stimulat similar calcium spiking patterns in mouse oocytes but by separate mechanisms. *Development* 119: 179–189 (1993).
Dale, B. et al. Injection of a soluble sperm fraction into sea–urchin eggs triggers the cortical granule reaction. *Experientia* 41: 1068–1070 (1993).
Dale, B. et al. Injection of a soluble sperm fraction into sea–urchin eggs triggers the cortical granule reaction. *Experientia* 41: 1068–1070 (1985).
Dozortsev, D. et al. Sperm–associated oocyte–activating factor is released from the spermatozoon within 30 minutes after injection as a result of the sperm–oocyte interaction. *European Society for Human Reproduction and Embryology* 12: 2892–2796 (1997).
Duesbery, N. S. et al. CENP–E is an esstential kinetochore motor in maturing oocytes and is masked during Mos–dependent, cell cycle arrest at metaphase II. *Proc. Natl. Acad. Sci. USA* 94: 9165–9170 (1997).
Dupont, G. et al. Phospholipase C in mouse oocytes: characterization of βand γisoforms and their possible involvement in sperm–induced $Ca^{2+}$ signalling. Biochem J 316: 583–591 (1996).
Foltz, K. R. & Shilling, F. M. Receptor–mediated signal transduction and egg activation. *Zygote* 1: 276–279 (1993).
Homa, S.T. & Swann, K. A cytosolic sperm factor triggers calcium oscillations and membrane hyperpolarizations in human oocytes. *Hum. Reprod.* 9: 2356–2361, (1994).
Iwao, Y. & Fujimura, T. Activation of Xenopus eggs by RGD–containing peptides accompanied by intracellular $Ca^{2+}$ release. *Dev. Biol.* 177: 558–567 (1996).

(List continued on next page.)

Primary Examiner—Deborah J. Reynolds
Assistant Examiner—Peter Paras, Jr.
(74) Attorney, Agent, or Firm—Jones Day

(57) ABSTRACT

The invention provides a microinsertion-based, transcomplementation method of in vitro oocyte activation useful to identify properties of sperm-borne oocyte-activating factor(s) (SOAF) and ooplasmic interactions with sperm components at fertilization. The invention provides at least one detergent-insoluble heat-sensitive component of the perinuclear matrix of a spermatozoon ($SOAF_m$) that acts coordinately with at least one heat-stable submembrane sperm component. $SOAF_m$ is solubilized in vitro ($SOAF_s$) under reducing conditions similar to those encountered in the ooplasm. By the method of the invention, the failure of heat-inactivated demembranated sperm heads to activate an egg is rescued by coinsertion of $SOAF_s$ into an oocyte. $SOAF_s$ is protease-sensitive and is liberated from demembranated heads in a temperature-dependent manner that inversely correlates with the ability of demembranated sperm heads to activate oocytes.

20 Claims, 5 Drawing Sheets

OTHER PUBLICATIONS

Kimura, Y. & Yanagimachi, R. Intracytoplasmic sperm injection in the mouse. *Biol. Reprod.* 52: 709–720 (1995).

Kimura, Y. et al. Analysis of mouse oocyte activation suggests the involvement of sperm perinuclear material. *Biol Reprod.* 58: 1407–1415 (1998).

Kline, D. & Kline. J. T. Repetitive calcium transients and the role of calcium in exocytosis and cell cycle activation in the mouse egg. *Dev. Biol.* 149: 80–89 (1992).

Kuretake, S. et al. Fertilization and development of mouse oocytes injected with isolated sperm heads. *Biol. Reprod.* 55: 789–795 (1996). Rodman, T. C. Chromosomes of the forst polar body in mammalian meiosis. *Exp. Cell Res.* 68: 205–210 (1971).

Marston, J. H. & Chang, M. C. The fertilizable life of ova and their morphology following delayed insemination in mature and immature mice. *J. Exp. Zool.* 155:237–252 (1964).

Meng, L. & Wolf, D. P. Sperm–induced activation in the rhesus monkey: nuclear and cytoplasmic changes following intracytoplasmic sperm injection. *Hum. Reprod* 12: 1062–1068 (1997).

Moses, R. M. & Kline, D. Release of mouse eggs from metaphase arrest by protein synthesis inhibition in the absence of a calcium or microtubule assembly. *Mol. Reprod. Dev.* 41: 264–273 (1995).

Palermo, G. D. Human sperm cytosolic factor triggers $Ca^{2+}$ oscillations and overcomes activation failure of human oocytes. *Mol. Hum. Reprod.* 367–374 (1997).

Parrington, J. et al. Calcium oscillations in mammalian eggs triggered by a soluble sperm protein. *Nature* 379: 364–368 (1996).

Perry, A. C. F. et al. A novel trans–complementation assay suggests full mammalian oocytes is coordinately initiated by multiple, submembrane sperm components. *Biol Reprod.* 60: 747–755 (1999).

Shilling, F. M. et al. Evidence for both tyrosine kinase and G–protein coupled pathways leading to starfish egg activation. *Dev. Biol* 166:34–58 (1994).

Stice, S. L. & Robl, J. M. Activation of mammalian oocytes by a factor obtained from rabbit sperm. *Mol. Reprod. Dev.* 25: 272–280 (1990).

Sutovsky, P. et al. The removal of the sperm perinuclear theaca and its association with the bovine oocyte surface during fertilization. *Dev. Biol.* 188: 75–84 (1997).

Swann, K. A cytosolic sperm factor stimulates repetitive calcium increases and mimics fertilization in hamster eggs. *Development* 110: 1295–1302 (1990).

Swann K. & Lai, F. A. A novel signalling mechanism for generating $Ca^{2+}$ oscillations at fertilization in mammals. *Bioessays* 19: 371–378 (1997).

Toshimori, K. et al. A monoclonal antibody, MN13, that recognizes specifically a novel substance between the post-acrosomal sheath and the overlying plasma membrane in the mammalian sperm head. *Mol. Reprod. Dev.* 29: 289–293 (1991).

Usui, N. Morphological differences in nuclear materials released from hamster sperm heads at an early stage of incorporation into immature oocytes, mature oocytes, or fertilized eggs. *Mol. Reprod. Dev.* 44: 132–140 (1996).

Whittingham, D. G. & Siracusa, G. The involvement of calcium in the activation of mammalian oocytes. *Exp. Cell Res.* 113: 311–317 (1978).

Williams, C. J. et al. Role of G–proteins in mouse egg activation: stimulatory effects of acetylcholine on the ZP2 and ZP2f conversion and pronuclear formation in eggs expressing a functional m 1 muscarinic receptor. *Dev. Biol.* 15: 288–296 (1992).

Wu, H. et al. Injection of porcine sperm factor induces activation of mouse eggs. *Mol. Reprod. Dev.* 49: 37–47 (1998).

Yanagimachi, R. & Noda, Y. D. Electron microscope studies of sperm incorporation into the hamster egg. *Am. J. Anat.* 128: 429–462 (1970).

Yanagimachi, R. The Physiology of Reproduction, Second Ed., New York: Raven Press: 189–317 (1994).

INITIATION OF FULL MAMMALIAN OOCYTE ACTIVATION BY MULTIPLE SPERM COMPONENTS

This application claims the benefit of U.S. Provisional Patent Application, Serial No. 60/115,118, filed Jan. 8, 1999.

The U.S. Government has a paid-up license in this invention and the right in limited circumstances to require the patent owner to license others on reasonable terms as provided for by the terms of contract numbers R01-HD-03402 and R01-HD-34362 awarded by The National Institute of Child Health and Human Development, the National Institutes of Health, Public Health Services.

BACKGROUND OF THE INVENTION

The invention relates to the activation of a mammalian oocyte by a coordinated activity of one or more heat-sensitive constituents and at least one heat-stable constituent of a spermatozoon submembrane perinuclear matrix.

For fertilization to be successful, sperm and egg components must mutually initiate the network of events required for full embryonic development to produce normal young. The subset of these events that immediately follow sperm-egg fusion and that leads up to the mingling of sperm and egg chromosomes is collectively termed oocyte activation [R. Yanagimachi in The Physiology of Reproduction, Second Ed., New York, Raven Press, pp. 189–317 (1994)]. The interplay between fertilizing sperm and egg factors that initiate oocyte activation is still unclear although, often by analogy with other systems, several components of potential signaling pathways have been identified within mature, metaphase-arrested oocytes (i.e., of the type encountered by a fertilizing spermatozoon.) Experimental evidence supports G protein mediated pathways in the eggs of both invertebrates [F. M. Shilling, et al., *Dev. Biol* 166, 34–58 (1994)] and vertebrates [C. J. Williams, et al., *Dev. Biol.* 15, 288–296 (1992)] and of phospholipase C-mediated signal transduction, also in the case of both invertebrates [D. J. Carroll, et al., *J. Cell Biol.* 138, 1303–1311 (1997)] and vertebrates [G. Dupont, et al., Biochem J. 316, 583–591 (1996)]. The breadth of this potential signaling repertoire may reflect functional redundancy with multiple pathways each capable of eliciting full activation [G. Dupont, et al., (1996)]. It is likely that $Ca^{2+}$ mobilization is pivotal to at least one of these pathways [M. J. Berridge, *Nature* 361, 315–325 (1993)].

The mechanism by which oocyte activation is initiated is broadly described in two models: 1) transmembrane signaling transduction across the oolemma upon sperm-egg binding/fusion, and 2) the introduction of a sperm soluble factor that initiates activation within the ooplasm [B. Dale, et al., *Experientia* 41, 1068–1070 (1985); K. Swann, *Development* 110, 1295–1302 (1990); and K. R. Foltz and F. M. Shilling, *Zygote* 1, 276–279 (1993)]. The models are not mutually exclusive. The first relies in large part on the observation that oocytes from vertebrates and nonvertebrates contain signal-transducing components that, in other systems described above, respond to altered states in transmembrane receptors. So far, few "candidate receptors" have been identified, perhaps the strongest belonging to the RGD-sensitive integrins resident on the plasma membrane of Xenopus and mouse eggs [E. A. C. Almeida, et al., *Cell* 81, 1095–1104 (1995); and Y. Iwao and T. Fujimura, *Dev. Biol.* 177, 558–567 (1996)]. Recently, it has been shown that when mouse spermatozoa are microinjected directly into the ooplasm, circumventing gamete surface-surface interactions, full activation nevertheless occurs, with development of resulting embyros to term after transfer [Y. Kimura and R. Yanagimachi, *Biol. Reprod.* 52, 709–720 (1995); S. Kuretake, et al., *Biol. Reprod.* 55, 789–795 (1996); and Y. Kimura, et al., *Biol. Reprod.* 58, 1407–1415 (1998)]. In particular, it has been shown that, when microinjected into mouse oocytes, demembranated sperm heads are capable of eliciting full activation and embryo development to term [S. Kuretake, et al., (1996); and Y. Kimura, et al., (1998)]. This activating function resides in the sperm head, not the tail, and that it appears during spermiogenesis in the mouse [Y. Kimura, et al., (1998)]. These findings are consistent with the second hypothesis, that a sperm factor can initiate activation by interacting directly with the ooplasm. It has been suggested that sperm cytosolic components from a wide variety of mammalian species, including the mouse, hamster, monkey, rabbit, and human can play such a role [K. Swann, (1990); S. L. Stice and J. M. Robl, *Mol. Reprod. Dev.* 25, 272–280 (1990); S. T. Homa and K. Swann, *Hum. Reprod.* 9, 2356–2361, (1994); L. Meng and D. P. Wolf, *Hum. Reprod* 12, 1062–1068 (1997); and K. Swann and F. A. Lai, *Bioessays* 19, 371–378 (1997)]. The sperm components at the center of several previous studies can be readily liberated by brief sonication or simple freeze-thawing, although in some cases their ability to activate is inferred from the similarity between induced intracellular $Ca^{2+}$ mobilization and that observed at fertilization. Unfortunately, this is potentially misleading for two reasons: 1) it is possible that not all normal activation pathways require or exhibit $Ca^{2+}$ mobilization [R. M. Moses and D. Kline, *Mol. Reprod. Dev.* 41, 264–273 (1995)] and, conversely, 2) factors may be identified that can cause $Ca^{2+}$ mobilization in oocytes but play no role in normal fertilization or embryonic development.

Regardless of the mechanism(s) of oocyte activation, it is known that there are instances in which human and/or other mammal spermatozoa are not capable of activating oocytes. Therefore, there is still a need to identify constituents of spermatozoa that lead to full oocyte activation, sufficient for the birth of live young.

SUMMARY OF THE INVENTION

The invention provides a method of identifying certain properties of sperm-borne oocyte-activating factor(s) (SOAF) responsible for triggering full oocyte activation. It was predicted that to account for SOAF activity during oocyte activation by a demembranated spermatozoon head, an apparently detergent-insoluble sperm component with the properties of SOAF would have to be responsive to ooplasmic factors during fertilization. By the method of the invention, such a sperm component has been identified. To demonstrate the properties of this sperm component, the method of the invention includes in vitro activation of oocytes by a microinsertion-based "trans-complementation" assay, i.e., the failure of a heat-inactivated demembranated mature spermatozoon head to activate an egg is rescued by coinsertion of a soluble factor isolated from a non-heat-inactivated demembranated spermatozoon head under reducing conditions. Thus, by the method of the invention, mature spermatozoa are demembranated under conditions that provide demembranated spermatozoa heads comprising nuclei and matrix-bound perinuclear material that retain oocyte activation activity if injected into the ooplasm of oocytes. A soluble factor ($SOAF_s$) is extracted from an aliquot of the demembranated spermatozoa heads by incubation in a physiological medium containing a reducing agent such as, but not limited to, dithiothreitol (e.g., about 15 millimolar, mM) or reduced glutathione (e.g., about 10 mM) at about 0° C. to about 37° C. for about 30 minutes. Another aliquot of the demembranated spermatozoa heads is heat-treated in a physiological medium, preferably under reducing conditions, at a temperature sufficient to abolish oocyte activation activity (e.g., about 44° C. to about 100° C.). Co-insertion of an inactivated demembranated spermatozoon head and an aliquot of the soluble factor into an unfertilized oocyte, results in activation of the oocyte. Thus, $SOAF_s$ "rescues" the activity of the inactivated demembranated spermatozoon head to activate an oocyte.

A feature of the invention is the discovery that $SOAF_s$ is trypsin-sensitive and is liberated from the matrix-bound perinuclear material of the demembranated spermatozoa in a temperature-dependent manner. Moreover, the ability of the demembranated spermatozoa to activate oocytes is also temperature-dependent and is inversely correlated with the liberation of $SOAF_s$. The activity of $SOAF_s$ to "rescue" heat-inactivated demembranated spermatozoa heads in oocyte activation is abolished by heat-treatment at about 44° C. to about 100° C. Without being bound by theory, it is believed that the sperm-borne oocyte-activation factor identified by the invention is a matrix-bound sperm-borne oocyte-activating factor ($SOAF_s$) that transitions to a soluble form, $SOAF_s$, under reducing conditions such as those present in the ooplasm of an oocyte. In contrast to previously-identified cytosolic factors from mouse or hamster sperm which induce resumption of meiosis when injected alone into oocytes, insertion into an oocyte of $SOAF_s$ alone does not activate the oocyte. Therefore, the $SOAF_s$ isolated by this invention appears to be distinct from these previously-identified cytosolic factors.

$SOAF_s$ is not highly species specific, as the loss of activation function in heat-inactivated mouse spermatozoa could be efficiently rescued in $SOAF_s$ samples derived from demembranated sperm from the human, pig, bull and hamster. As described above, there are instances in which human or other mammalian spermatozoa used for artificial insemination, such as in in vitro fertilization (IVF) procedures, are not capable of oocyte activation. Where the lack of oocyte activation activity is due to a reduced amount of sperm-oocyte activating factor(s), microinsertion of such a soluble human SOAF factor could be used to rescue oocyte activation activity.

Thus, the invention provides a spermatozoon-derived oocyte activating factor which acts coordinately with a heat-stable submembrane component of a spermatozoon to activate a mammalian oocyte. The sperm-derived oocyte activating factor is insoluble in a detergent and is retained in the perinuclear matrix of a demembranated spermatozoon head. The factor has an oocyte activating activity in coordination with the heat-stable submembrane component that is abolished by heat treatment at about 44° C. to about 100° C., and at least a portion of the factor is solubilized by incubation of a demembranated sperm head in a physiological medium containing a reducing agent at about 0° C. to about 37° C.

In summary, the invention provides a method for identifying the contribution to oocyte activation of spermatozoa components that are known to breach the oolemma at fertilization (i.e., components of a demembranated spermatozoon head). By the method of the invention, we demonstrate that oocyte activation by demembranated spermatozoa proceeds via the coordinated action of at least two spermatozoa head components, including an extremely heat-stable component retained by demembranated spermatozoa heads, and a relatively detergent-insoluble matrix component ($SOAF_s$) that can be solubilized in vitro under reducing conditions, such that a $SOAF_m \rightarrow SOAF_s$ transition can be demonstrated. Without being bound by theory, it is believed that mammalian oocyte activation sufficient for full development is initiated via essentially insoluble (as opposed to cytosolic) spermatozoa head components that become solubilized in response to the ooplasm when introduced into the egg at fertilization.

DETAILED DESCRIPTION OF THE INVENTION

To initiate normal embryonic development, an egg must receive a signal to become activated at fertilization. The most easily recognizable visible indications of egg activation in mammals are the exocytosis of cortical granules and the resumption of meiosis. The egg arrested at metaphase of the second meiosis before fertilization completes the meiosis after sperm-egg fusion. The resulting haploid complement of chromosomes then transforms into an egg pronucleus. Meanwhile, the sperm nucleus decondenses and transforms into a sperm pronucleus. DNA synthesis (chromosome duplication) begins in both the egg and sperm pronuclei several hours after sperm-egg fusion. The fully developed sperm and egg pronuclei come into close approximation at the center of the egg, their nuclear envelopes disintegrate and their chromosomes mingle prior to the first mitotic division. The mingling of chromosomes (syngamy) can be considered as the end of fertilization and the beginning of embryonic development.

It has previously been shown that detergent insoluble material in (demembranated) sperm heads can elicit full oocyte activation when microinjected into mouse oocytes, leading to the birth of live young, and that this activating function resides in the sperm head, not the tail. We have now discovered certain properties of a sperm-borne oocyte-activating factor(s) (SOAF) responsible for triggering this full activation.

We have discovered and demonstrate herein the presence in mouse sperm of at least two molecular species that coordinately induce oocyte activation from structures known to enter the ooplasm at fertilization (i.e., a demembranated spermatozoon head including the nucleus and perinuclear material). While not being bound by theory, it is believed that the properties of SOAF described herein below suggest a novel mechanism of mammalian oocyte activation that has partially been produced in vitro, as demonstrated below.

Figure 1:
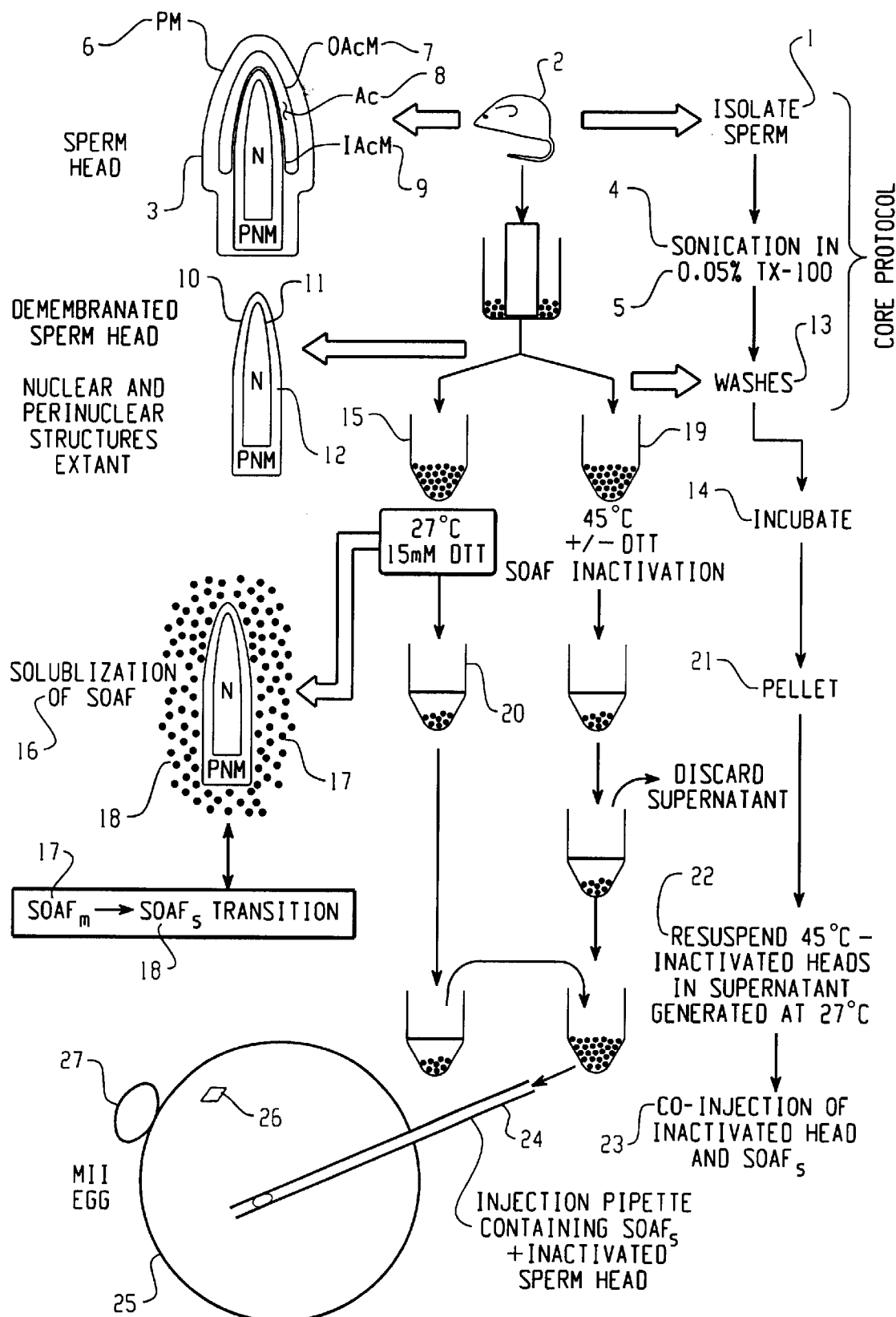
FIG. 1 is a diagrammatic outline of a method of transcomplementation of the invention. Topological representation of sperm heads is related to an experimental procedure that reproduces a transition from a perinuclear matrix-bound factor to a soluble form of the factor in vitro. Abbreviations: PM, plasma membrane; OAcM, outer acrosomal membrane; Ac, acrosome; IAcM, inner acrosomal membrane; N, nucleus; PNM, perinuclear matrix; MII, metaphase II.

To demonstrate this mechanism, we have developed a trans-complementation assay, illustrated diagrammatically in FIG. 1. By the method, spermatozoa are isolated 1 from a mammal 2, such as a mouse, hamster, boar, bull, and the like. The heads 3 of the spermatozoa are separated from the tails by a method such as sonication 4, and the spermatozoon head 3 is treated 5 either simultaneously or subsequently with a detergent such as, but not limited to, Triton X-100 to remove the plasma membrane 6 (PM), outer acrosomal membrane 7 (OAcM), the contents of the acrosome 8 (Ac) and the inner acrosomal membrane 9 (IAcM), resulting in a demembranated spermatozoon 10 that contains the nucleus 11 and the perinuclear structures (perinuclear matrix) 12. The demembranated spermatozoa 10 are then subjected to one or more washing steps 13. Incubation 14 of an aliquot 15 of the demembranated spermatozoa 10 in a physiological medium containing a reducing agent (such as 15 mM dithiothreitol, DTT, or 10 mM reduced glutathione, GSH) at about 0° C. to about 37° C. (for example, at about 27° C. or about 30° C.) for about 30 minutes solubilizes 16 a perinuclear matrix component which is referred to herein as $SOAF_m$ 17 to produce the soluble form $SOAF_s$ 18. Incubation 14 of an aliquot 19 of the demembranated spermatozoa 10 at a temperature of about 44° C. to about 100° C. abolishes oocyte activation activity resulting in inactive spermatozoa. Preferably, the aliquot 19 is incubated in a physiological medium in the presence of a reducing agent, such as DTT or GSH. After incubation the spermatozoa in the aliquots are pelleted 21. The supernatant 20 from the incubated aliquot 15 is collected. This supernatant contains the $SOAF_s$ The inactivated spermatozoa 22 from aliquot 19 are resuspended in the supernatant 20. An aliquot of the suspension containing $SOAF_s$ and at least one inactivated spermatozoon head is then injected 23 through a microinjection pipette 24 into an unfertilized metaphase II oocyte 25 (which contains a metaphase plate 26 and a first polar body 27). Co-insertion of the inactivated sperm head and the supernatant containing $SOAF_s$ results in activation of the oocyte. Therefore, the $SOAF_s$ rescues the activity of the inactive spermatozoon to activate the oocyte.

Thus, the method of trans-complementation of the invention is a method of in vitro activation of oocytes that comprises the steps of: (a) providing an unfertilized oocyte comprising ooplasm; (b) providing mature spermatozoa; (c) demembranating the spermatozoa under conditions that provide demembranated spermatozoa heads comprising nuclei and matrix-bound perinuclear material that retain oocyte activation activity if injected into the ooplasm of oocytes; (d) incubating a first aliquot of the demembranated spermatozoa heads in a physiological medium containing a reducing agent at about 0° C. to about 37° C. for about 30 minutes; (e) obtaining a supernatant from the incubated first aliquot; (f) incubating a second aliquot of the demembranated spermatozoa heads in a physiological medium at a temperature sufficient to abolish oocyte activation activity; (g) inserting an inactivated demembranated spermatozoon head from step (i) into the ooplasm of the oocyte; and (h) inserting a portion of the supernatant from step (e) into the ooplasm of the oocyte, wherein the insertion of the inactivated demembranated spermatozoon head and the portion of the supernatant result in activation of the oocyte.

In one embodiment of the method of the invention, the inactivated heads are inserted into the oocyte first. The oocytes may then be incubated at about 37° C. for 2 to 4 hours before subsequently being injected with an aliquot of the supernatant.

In another embodiment of the method of the invention, the insertion steps (g) and (h) are combined and comprise the substep of suspending the inactivated demembranated spermatozoa heads from the second aliquot in the supernatant from the first aliquot, and the insertion step comprises inserting a portion of the suspension containing the supernatant and an inactivated demembranated spermatozoon head into the ooplasm of the oocyte.

The steps of the method are now described in detail.

Preparation of Spermatozoa

Physiologically mature spermatozoa are required to activate oocytes. In mature spermatozoa, DNA is associated with basic proteins called protamines. In mammals, protamines are extensively cross-linked by disulfide bonds. This stabilizes the sperm nuclei and renders them very resistant to physical and chemical disruption. Cross-linking of nuclear protamines occurs mainly during transit of the spermatozoa through the epididymis. Thus, mammalian spermatozoa within the epididymis and in ejaculate (semen) are generally physiologically more mature than those within the testis, and are preferred in the methods of the invention, at least in mammals.

Mature spermatozoa from invertebrates and vertebrates are collected by methods known to those skilled in the art. For example, mature spermatozoa of rodents, such as mouse, golden (Syrian) hamster, guinea pig, rabbit, and the like, may be collected from caudae epididymes; whereas, in other species, such as humans, pigs, horses, bulls, goats, fowl, and the like, mature spermatozoa may be isolated from freshly ejaculated semen of fertile males. Spermatozoa of fish (e.g., swordtail, *Xiphophorus helleri*) and invertebrates, such as sea urchins (*Tripneustes gratilla*), may be collected from the testes of mature males.

An example of a method for obtaining spermatozoa from a cauda epididymis follows. A cauda epididymis is removed from a mature male mouse (approximately 8 weeks after birth or older). The blood and adipose tissue are removed from the surface of the cauda epididymis. It is then compressed to release a dense mass of spermatozoa. A drop (about 2 μL) of sperm mass is placed in the bottom of 1.5 ml polypropylene centrifuge tubes and overlaid with 0.5 ml of warm physiological medium (e.g., CZB medium, phosphate buffered saline, or isotonic saline). After about 10 to 20 minutes at 37° C., motile spermatozoa may be collected from the supernatant.

An example of a method for obtaining spermatozoa from semen follows. Freshly ejaculated human semen is allowed to liquefy for about 30 minutes at room temperature (about 25° C.). The semen is then diluted with about 10 ml of saline and filtered through about two layers of tissue paper to remove debris. The filtrate may then be centrifuged at 400×g for about 10 minutes, and the sedimented spermatozoa resuspended in a physiological solution at a desired concentration for the freeze-drying process.

Regardless of the method used for preparation of the spermatozoa, more than 50% of the recovered spermatozoa should be motile.

The spermatozoa so recovered are suspended in a physiological medium, such as CZB or NIM medium described further below, in preparation for further processing to obtain demembranated sperm heads.

Preparation of Demembranated Sperm Heads

Demembranated sperm heads are detergent-extracted heads that lack all membranes, including the plasma membrane and inner and outer acrosomal membranes, but retain the nucleus and perinuclear material. For example, sperm heads may be demembranated by treatment with Triton X-100. Triton X-100 is a well known non-ionic surfactant that is widely used for removal of membrane components under non-denaturing conditions. In the mouse, sperm heads demembranated by using Triton X-100 have been shown to be capable of activating oocytes, leading to normal embryonic development.

An exemplary method for demembranating sperm heads follows. An aliquot of a sperm suspension, prepared as above, is sonicated. For example, spermatozoa collected from caudae epididymes or semen, as above, may be suspended in 5 ml BM buffer (75 mM NaCl, 24 mM EDTA, and 50 mM Tris-HCl, pH 7.2) and sonicated for 30 seconds at 70%–80% output of a Biosonik sonicator (Bronwill Scientific, Rochester, N.Y.). Over 95% of spermatozoa are decapitated by this treatment. To demembranate the sperm heads, the sonicated sperm suspension is centrifuged at 700×g for 5 minutes, and the pellet is washed with BM buffer and then treated at room temperature for 5 minutes with 1% Triton X-100 in NIM medium. (NIM medium consists of 123.0 mM KCl, 2.6 mM NaCl, 7.8 mM NaH$_2$PO$_4$, 1.4 mM KH$_2$PO$_4$, 3 mM Na$_2$EDTA, having a pH of 7.2). The heads are then rinsed thoroughly with NIM medium in preparation for further processing.

The Recipient Unfertilized Oocytes

Recipient oocytes may be obtained, for example, by inducing an animal to ovulate or super-ovulate by injections of gonadotrophic hormones (for example, sequential administration of equine and human chorionic gonadotropin) and surgical harvesting of oviductal ova shortly after the expected time of ovulation (e.g., 13–15 hours after injection of human chorionic gonadotrophic in the mouse). Alternatively, ovarian oocytes are collected and cultured in a medium to allow their maturation, as is known to those skilled in the art. An example of preferred culture medium is modified Eagle's medium (MEM) supplemented with bovine serum albumin (BSA), as described in Downs, S. M. and A. M. Mastropolo, *Develop. Biol.* 162: 154–168, 1994 for mouse oocytes.

Insertion of Demembranated Spermatozoon Head Into Recipient Oocyte

The following is an exemplary method of microinjection of a demembranated sperm head suspended in supernatant into a recipient oocyte. A piezo electrically-driven micropipette is used. A suitable piezo electric driving unit is sold under the name of Piezo Micromanipulator/Piezo Impact Drive Unit by Prime Tech Ltd. (Tsukuba, Ibaraki-ken, Japan). The unit utilizes the piezo electric effect to advance, in a highly controlled, rapid manner, the (injection) pipette holder a very short distance (approximately 0.5 μm). The intensity and duration of each pulse can be varied and are regulated by a control unit.

For injection into an oocyte, a single spermatozoon head is drawn deeply into an injection pipette having a short, flat tip with an inner diameter of about 5 μm housed in the piezo electrically-actuated unit according to the instructions of the vendor.

Throughout the injection of the sperm head (nucleus), the oocyte is anchored by a conventional holding pipette. The tip of the injection pipette containing a selected sperm head is brought into intimate contact with the zona pellucida of an oocyte and several piezo pulses (using controller setting scales of intensity 1–5, speed 4–6) are applied to advance the pipette while maintaining a light negative pressure within. When the tip of the pipette has passed through the zona pellucida, the resultant zona plug is expelled into the perivitelline space and the sperm head is pushed forward until it is near the tip of the pipette. The pipette tip is then apposed to the plasma membrane and advanced (toward the opposite face of the oocyte) and the holding pipette almost reaches the opposite side of the cortex of the oocyte. The oocyte plasma membrane is now deeply invaginated around the tip of the injection needle. Upon application of one to two piezo pulses (intensity 1–2, speed 1), the oolemma is punctured at the pipette tip, as indicated by a rapid relaxation of the oolemma, which may be clearly visible. The sperm head is then expelled into the ooplasm with a minimum amount (about 6 pL) of accompanying medium. The pipette is then gently withdrawn, leaving the newly introduced head within the cytoplasm of the oocyte. This method is performed briskly, typically in batches of 10–15 oocytes which at all other times are maintained in culture conditions.

Alternative microinjection variants, in which a conventional injection pipette is employed, may be used to inject sperm heads. An example of a suitable microinjection method employing a conventional pipette, for injecting a sperm head into hamster oocyte, is described in Yanagida, K., Yanagimachi, R., Perreault, S. D. and R. G. Kleinfeld, *Biology of Reproduction* 44, 440–447 (1991), the disclosure of which pertaining to such method is hereby incorporated by reference.

Development of Embryos to Produce Viable Fetuses and Offspring

Following pronucleus formation, the embryo may be cultured in vitro until it reaches the 2–8 cell stage or morula/blastocyst stage, at which time the embryo may be transferred into the oviduct or uterus of a foster mother. Solubilization of SOAF$_s$ from the Perinuclear Matrix.

Figure 5:
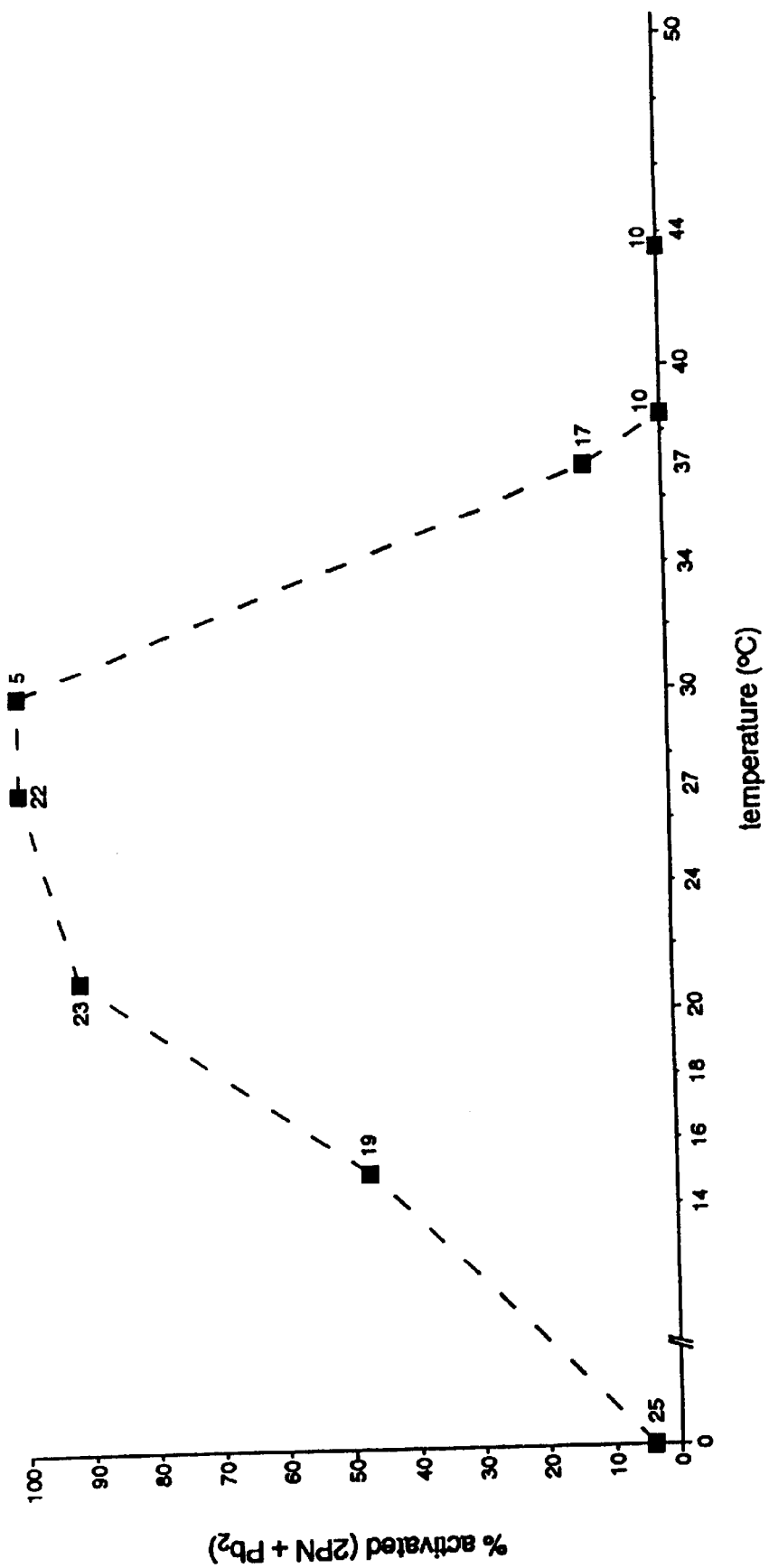
FIG. 5 is a graphic illustration of the liberation of $SOAF_s$ in response to temperature, demonstrated by its oocyte activating activity when coinserted into an oocyte with a heat-inactivated demembranated spermatozoon. The number of successful oocyte injections for each point is indicated. 2PN, two pronuclei; $Pb_2$, second polar body.

SOAF$_s$ is liberated from the perinuclear matrix in response to temperature, as illustrated in FIG. 5. Supernatants generated by heating demembranated sperm heads over a range of temperatures in a physiological medium in the presence of a reducing agent such as DTT or GSH can be tested for their ability to rescue heat-inactivated heads to activate oocytes in the trans-complementation assay described above. The reducing agent is preferably about 15 mM DTT or 10 mM GSH. The graphical plot illustrated in FIG. 5 shows that a small amount of SOAF$_s$ (as measured by the ability of a standard aliquot of the supernatant to rescue heat-inactivated heads heated to approximately 48° C. for 30 minutes and activate oocytes in the trans-complementation assay) is liberated at 0° C. and that the concentration of $SOAF_s$ in the supernatant increases with temperature to a maximum of about 30° C. For example, at about 15° C., the concentration of $SOAF_s$ released into the supernatant is sufficient to activate about 50% of the oocytes surviving injection. At about 20° C., the concentration of $SOAF_s$ released into the supernatant is sufficient to activate about 90% of the oocytes surviving injection. At both 27° C. and 30° C., the concentration of $SOAF_s$ released into the supernatant is sufficient to activate 100% of the oocytes surviving injection. The concentration of released $SOAF_s$ then decreases as the temperature increases until about 37° C., where the concentration is sufficient to activate about 10% of the oocytes. Essentially no $SOAF_s$ activity can be demonstrated at temperatures over about 39° C.

Figure 2:
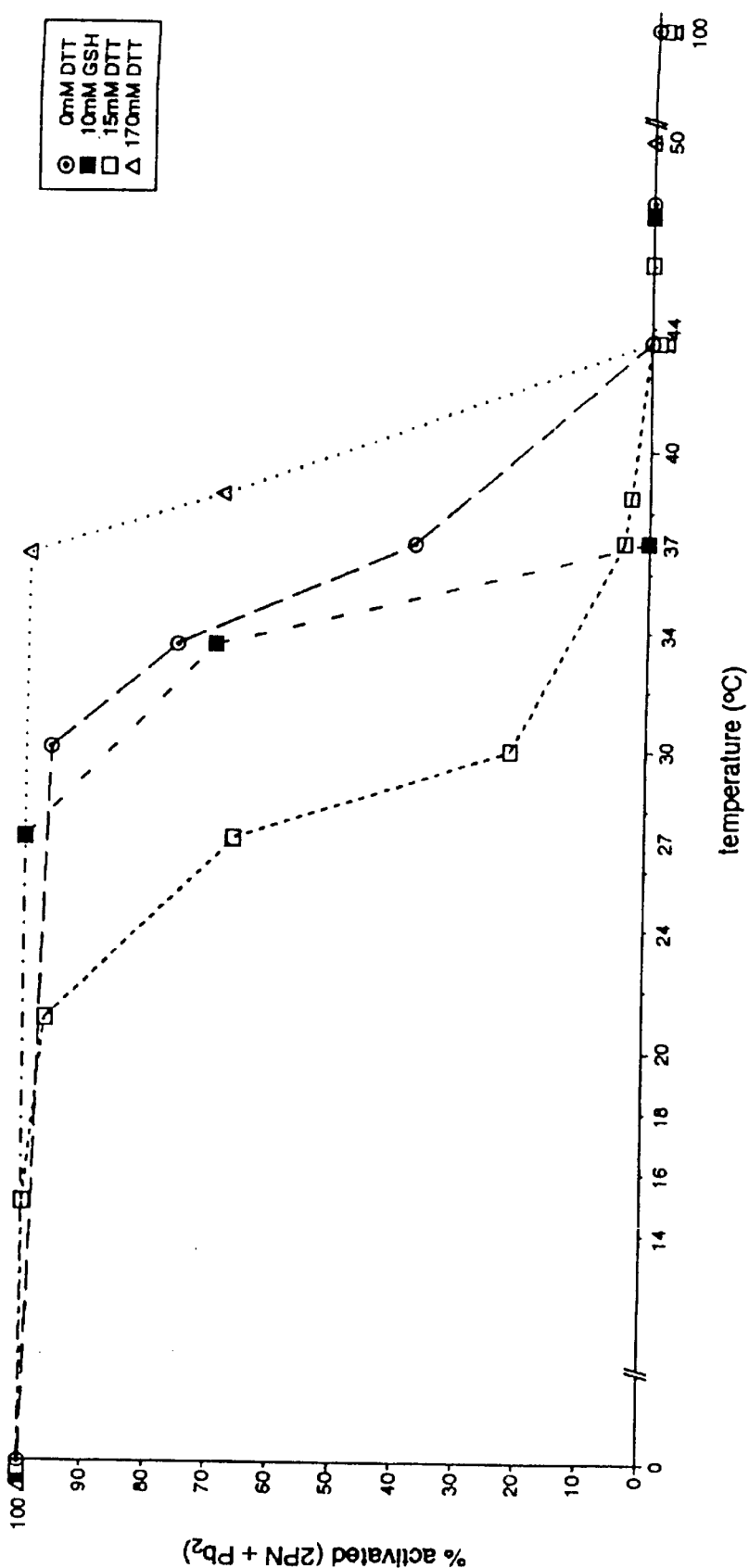
FIG. 2 is a graphic representation of the ability of demembranated sperm heads to activate oocytes, showing that the activity is temperature dependent and is affected by redox potential.

The Temperature and Redox Dependency of the Ability of Demembranated Sperm Heads to Activate Oocytes As illustrated in FIG. 2, demembranated spermatozoa heads incubated at different temperatures from about 0° C. to about 37° C. progressively lose the ability to active oocytes. This loss of activity is affected by the redox potential and is inversely correlated with the temperatures at which the concentration of SOAF, released into the supernatant increases. To inactivate demembranated heads, the preferred incubation is in a physiological medium comprising a reducing agent. For example, the reducing agent may be dithiothreitol or reduced glutathione. In one embodiment, the DTT is present in the medium at about 15 mM to about 170 mM. In another embodiment, the GSH is present in the medium at about 10 mM. Preferably the inactivation is accomplished by incubation of the demembranated spermatozoa heads at about 44° C. to about 100° C. For example, samples may be incubated at about 44° C. to about 48° C. for about 30 minutes, or at about 100° C. for about 10 minutes.

Properties of the Spermatozoon-derived Oocyte Activation Factor (SOAF) Identified by the Invention The SOAF factor identified by the invention acts coordinately with a heat-stable submembrane component of a spermatozoon to activate a mammalian oocyte. The factor is insoluble in a detergent and is retained in the perinuclear matrix of a demembranated spermatozoon head. The factor has an oocyte activating activity in coordination with the heat-stable submembrane component that is abolished by heat treatment at about 44° C. to about 100° C., preferably in a reducing medium, wherein at least a portion of the factor is solubilized by incubation of a demembranated sperm head in a physiological medium containing a reducing agent at about 0° C. to about 37° C. The oocyte-activation activity of the factor is abolished by protease treatment, for example by treatment with trypsin at about 100 µg/ml (Table 1). Because of the heat- and protease-sensitivity of the factor, it is believed to be proteinaceous.

The factor is distinct from the cytosolic sperm factors whose prototype is glucosamine 6-phosphate isomerase-oscillin, because insertion of the solubilized factor alone, without inactivated demembranated sperm heads, does not activate the oocyte.

In summary, by the invention it has been demonstrated that oocyte activation by demembranated mammalian sperm heads is heat sensitive; it is abolished by treatment at or above temperatures of approximately 45° C. The invention thus provides an injection assay for trans-complementation of inactivated sperm heads by solubilized (i.e., not cytosolic) factors. It has been demonstrated an activity, that of the factor SOAF, that is solubilized by exposure to a reducing environment and that, in the invention trans-complementation assay, is obligate in triggering full oocyte activation sufficient for the birth of normal young. It has been demonstrated that the factor responsible for this activity is proteinaceous and that it too is inactivated by exposure to temperatures above 45° C. Although obligate for activation in this system, $SOAF_s$ is not sufficient for it, requiring at least one additional sperm head component that is extremely heat stable. Hence, neither 48° C.-heated heads nor SOAF, alone is sufficient to elicit activation when injected separately, whereas they do when coinjected.

It has been demonstrated herein that spermatozoa contain at least two distinctive functions capable of initiating oocyte activation: a cytosolic activity and a complex submembrane activity that includes SOAF. It has been demonstrated herein the coexistence of these functions in both the mouse and hamster. While not being limited to theory, we believe that the non-invention cytosolic function corresponds to previously described activities whose prototype is glucosamine 6-phosphate isomerase-oscillin [J. Parrington, et al., *Nature* 379, 364–368 (1996); H. Wu et al., *Mol. Reprod. Dev.* 49: 37–47 (1998)].

Again, while not being limited by theory, it is believed that it is possible that although sperm possess two distinct functions capable of inducing activation, one of the functions in fact plays a different physiological role in fertilization. This is plausible given the involvement of an additional key $Ca^{2+}$ mobilization step within sperm during the fertilization process: the induction of acrosomal exocytosis. This $Ca^{2+}$-dependent process is apparently mediated via T-type, voltage-sensitive $Ca^{2+}$ channels [C. Arnoult et al., *PNAS USA* 93: 13004–13009 (1996)]. However, such channels mediate small, transient $Ca^{2+}$ influxes into the acrosome, rather than the sustained, high levels observed during acrosomal exocytosis. Spermatozoa may therefore possess effectors of elevated $Ca^{2+}$ levels (which work by interacting, perhaps indirectly, with inositol 1,4,5-triphosphate receptors) that, when injected into oocytes, cause $Ca^{2+}$ oscillations and activation. This would have parallels with the fashion in which the nonphysiological agent $SrCl_2$ induces $Ca^{2+}$ oscillations and oocyte activation. It is believed that the cytosolic activity found by others would be far more likely to be involved in acrosomal exocytosis than a relatively insoluble ensemble (which includes SOAF) derived from the nucleus/perinuclear matrix. Moreover, neither our previous findings nor those presented herein, nor any work that we are aware of, has demonstrated cytosolic oocyte-activating factors in acrosome-reacted spermatozoa or in any sperm compartment known to traverse the oolemma following membrane fusion at fertilization.

In contrast, the presence in mouse sperm of at least two molecular species that coordinately induce oocyte activation, has been demonstrated herein from structures known to enter the ooplasm at fertilization. Therefore, the properties of SOAF described herein suggest a previously undescribed mechanism of mammalian oocyte activation that we have partially reproduced in vitro, as represented in FIG. 1.

In this molecular model, $SOAF_s$ is generated from $SOAF_m$ immediately after sperm-egg fusion, consistent with the rapid dispersal of perinuclear material on gamete fusion [R. Yanagimachi (1994); R. Yanagimachi and Y. D. Noda, *Am. J. Anat.* 128, 429–462 (1970); N. Usui, *Mol. Reprod. Dev.* 44, 132–140 (1996); and P. Sutovsky et al., *Dev. Biol.* 188: 75–84 (1997)]. The immediate $SOAF_m \rightarrow SOAF_s$ transition generated on contact of the perinuclear matrix with the reducing environment of the ooplasm would rapidly liberate $SOAF_s$, thereby initiating the first steps of activation. This $SOAF_m \rightarrow SOAF_s$ transition is simulated in vitro by the incubation of demembranated sperm under reducing conditions. It is as yet unclear whether physiologically active, native SOAF substantially exists (in some species, at least) as $SOAF_s$ in acrosome-reacted spermatozoa prior to gamete fusion, although the existence of such material would clearly favor the rapid delivery of an activating signal. Otherwise, $SOAF_m$ would presumably reside on the periphery of the perinuclear matrix so that it immediately engaged with the ooplasm at fertilization. Few, if any, molecular markers with this localization have been reported, with the possible exception of an epitope recognized by monoclonal antibody MN13 [K. Toshimori et al., *Mol. Reprod. Dev.* 29: 289–292 (1991)]. However, synchrony between mouse sperm perinuclear matrix deposition [Bellvé et al. in Hanman JF (ed.), Mechanism and Control of Animal Fertilization. New York: Academic Press; 1983, pp. 55–137] and innate activating ability [Y. Kimura et al., (1998)] is consistent with a perinuclear localization for SOAF. After fertilization, subsequent "waves" of $SOAF_s$ could potentially be provided through the continued solubilization of $SOAF_m$ as the perinuclear matrix became progressively excoriated by the ooplasm. In this scenario, the sperm head is a "SOAF bomb."

Without being bound by theory, we believe our observations are perhaps best explained if the synergistic action of each molecular species ($SOAF_s$ and the heat-stable component) worked by stimulating convergent activation pathways within the oocyte. Since inactivated sperm heads prime oocytes for activation by $SOAF_s$ for several hours following their injection, any signal originating from them would either be continuous or be "memorized" by the ooplasm for that duration. The development of the trans-complementation assay of the invention is further enabling us to dissect ooplasmic interactions with sperm components at fertilization and with somatic chromatin following in vitro nuclear transfer.

EXAMPLES

The following examples illustrate the invention. In particular, the examples illustrate the trans-complementation assay for rescuing the oocyte-activation activity of heat-inactivated demembranated spermatozoa by a solubilized sperm membrane component. The examples further illustrate certain physical and chemical properties of the sperm-borne oocyte-activation factor. For purposes identification of properties of sperm-borne oocyte-activation factors of the invention, as described below, an oocyte was considered to be activated if it exhibited both a male and a female pronucleus (2PN) and a second polar body ($Pb_2$).

The examples described herein are not intended to be limiting, as other examples of embodiments of the invention would readily be recognized by those skilled in the art.

Media and Reagents.

Harvested oocytes were collected into CZB medium (Chatot, et al., 1989. *J. Reprod. Fert.* 86:, 679–688). CZB medium comprises 81.6 mM NaCl, 4.8 mM KCL, 1.7 mM $CaCl_2$, 1.2 mM $MgSO_4$, 1.8 mM $KH_2PO_4$, 25.1 mM $NaHCO_3$, 0.1 mM $Na_2EDTA$, 31 mM Na lactate, 0.3 mM Na pyruvate, 7 U/ml penicillin G, 5U/ml streptomycin sulfate, and 4 mg/ml bovine serum albumin. CZB-H medium used to remove the cumulus mass from oocytes was comprised of CZB medium buffered with 20 mM Hepes, pH 7.4, containing 0.1% (w:v) bovine testicular hyaluronidase (300 U/mg; ICN Biochemicals, Costa Mesa, Calif.) [Y. Kimura and R. Yanagimachi, *Biol. Reprod.* 52, 709–720 (1995)]. Mineral oil used in oocyte manipulations was obtained from Squibb & Sons, Princeton, N.J. Nuclear Isolation Medium (NIM) used in preparation of spermatozoa is comprised of 125 mM KCl, 2.6 mM NaCl, 7.8 mM $Na_2HPO_4$, 1.4 mM $KH_2PO_4$, 3.0 mM EDTA; pH 7.45 [S. Kuretake, et al., *Biol. Reprod.* 55, 789–795 (1996)]. Amine-modified latex beads used in place of sperm heads in some of the microinjection experiments (mean diameter 2.16 μm; Cat. no. L-0280) were obtained from Sigma Chemical Co., St. Louis, Mo.

Animals.

Animals used in this study were maintained within the guidelines of the Laboratory Animal Service at the University of Hawaii and those prepared by the Committee on Care and Use of Laboratory Animals of the Institute of Laboratory Resources National Research Council (DHEW publication no. [NIH] 80-23, revised in 1985). Animal-handling protocols were as reviewed and approved by the Animal Care and Use Committee at the University of Hawaii

Example 1
Preparation of Recipient Oocytes

Four- to 10-week-old B6D2F1 female mice were superovulated by consecutive intraperitoneal injections of 5 international units (IU) equine chorionic gonadotropin (eCG) and 5 IU of human chorionic gonadotropin (hCG) about 48 hours apart. About 14.5 to 16 hours after hCG injection, mature oocyte-cumulus complexes were collected from the oviducts. The cumulus cell mass was dispersed by immediate treatment in CZB-H containing 0.1% bovine testicular hyaluronidase (300 USP units/mg; ICN Pharmaceuticals, Costa Mesa, Calif.) for 5 to 10 minutes at room temperature. Cumulus-free oocytes were washed four times in CZB-H and transferred to a drop of CZB under mineral oil (Squibb & Sons, Princeton, N.J.), equilibrated in 5% (v:v in air) $CO_2$ at 37° C. Data were collected exclusively from oocytes for which primary microinjection was performed within 20 hours of hCG administration (the fertilizable life of ovulated mouse oocytes is more than 12 hours and delayed in vivo insemination of mice at 21 to 22 hours post-hCG injection gives rise to apparently normal zygotes at control rates) [J. H. Marston and M. C. Chang, *J. Exp. Zool.* 155, 237–252 (1964)].

Example 2
Preparation of Mouse Spermatozoa and Sperm-derived Material Core Protocol (Schematically Illustrated in FIG. 1)

Mature mouse spermatozoa were obtained by finely chopping the caudae epididymides of 1 to 3 freshly killed, 8- to 20-week-old male B6D2F1 mice in 600 μl NIM medium. The pH of all incubation cocktails was in the range of 7.07 to 7.50. Sperm suspensions were filtered through a single tissue paper (KimWipe; Kimberly-Clarke Corp., Roswell, Ga.) to remove tissue debris. All subsequent steps were performed at 0 to 4° C. The filtered sperm suspension was made 0.05% to 0.1% (v:v) with respect to Triton X-100 and subjected to three 5-second bursts of sonication (60% output) from a Biosonik sonicator (Bronwill Scientific, Rochester, N.Y.). This yielded greater than 99.9% decapitation and completely demembranated sperm heads [S. Kuretake, et al., *Biol. Reprod.* 55, 789–795 (1996). Sperm fragments were pelleted for 3 minutes at 20,000×g. Pellets were then washed thoroughly in approximately 2 ml NIM twice at 2° C. with pelleting times of 6 and 25 minutes, respectively (20,000×g). In experiments in which different sperm treatments were necessary, the washed sperm suspension was divided between fresh tubes prior to the final pelleting. Pellets were typically resuspended in 100 μl NIM (final sperm concentration was 2 to $10 \times 10^7$ sperm/ml) containing, where appropriate, dithiothreitol (DTT; pH 7.07–7.45) or 10 mM reduced glutathione (GSH). An aliquot of each test suspension was removed and held on ice just prior to, and for the duration of, the incubation. This sample served as a positive control. In most experiments, the remainder of the test suspension was incubated for 30 minutes at the desired temperature. In parallel, aliquots of the same freshly prepared batch of cells were inactivated by heating at or above 44° C., either for use as a negative control or with the test supernatant (see below). Most experiments included three incubations (positive and negative controls and the test) prepared from a single batch of cells. In all experiments, a parallel, mock incubation of NIM±DTT (or GSH) alone was used to generate a buffer control not exposed to spermatozoa. After incubation, spermatozoa were pelleted by spinning at 2° C. for 50 to 80 minutes at 20,000×g. The cell-free supernatant produced from the test suspensions was carefully removed to a fresh tube; control supernatants were generally discarded. Pellets were resuspended either in 20 μl buffer control (positive and negative controls) or in 20 μl test supernatant. Samples were injected on the day of preparation. Resulting suspensions were added to 20 μl 20% (w:v) polyvinylpyrrolidone (PVP; average Mr 360×10$^3$) for injection. Where appropriate, test supernatant in the absence of heads was mixed with an equal volume of 20% (w:v) PVP prior to injection. This procedure constituted the "Core Protocol" for the preparation of spermatozoa and sperm-derived material.

Example 3
Preparation of Spermatozoa from the Golden Hamster, Bull and Boar

Spermatozoa from the golden hamster were prepared from the single epididymis of a freshly killed, sexually mature male. Spermatozoa from other species were obtained from ejaculates and processed as described in the Core Protocol of Example 2. Sperm heads from the bull and boar were purified after a preliminary wash of ejaculates through a 0.25 M sucrose-NIM cushion. Resulting pellets corresponding to approximately half-strength ejaculate were resuspended in 10 ml NIM containing 0.2% to 0.4% (v:v) Triton X-100 and sonicated in eight 5-second bursts. Sonicated spermatozoa were diluted 3-fold in ice-cold NIM, and heads were pelleted through 30 ml 70% (w:v) sucrose-NIM in 5 ml batches by spinning at 16,000 rpm for 20 minutes in a Sorvall (Newtown, Conn.) RC-5 centrifuge. Pelleted sperm heads were washed three times in NIM resulting in a head:tail-fragment ratio of greater than or equal to about 10:1. Washed spermatozoa were finally resuspended in NIM-15 mM DTT yielding typical densities of 0.5 to 1.5×10$^9$ sperm/ml.

Example 4
Collection of Soluble Oocyte Activating Factor (SOAF$_s$) From Demembranated Spermatozoa Spermatozoa were decapitated/demembranated according to the method presented in the Core Protocol. The resulting sperm heads were incubated for 30 minutes in NIM-15 mM DTT at 0° C. to about 37° C. to liberate SOAF$_s$ from the sperm heads and into the suspension medium. Sperm heads were then pelleted at 2° C. for 50 to 80 minutes at 20,000×g. The resultant cell-free supernatant containing SOAF$_s$ was carefully removed.

Example 5
Treatment of SOAF$_s$ with Trypsin

A SOAF$_s$-containing supernatant was obtained by the method of Example 4, and 22.5 μl of the supernatant was added to 10-strength trypsin solutions (in NIM) to give various final trypsin concentrations (e.g.,50 or 100 μg/ml). Samples were incubated at 27° C. for 10 minutes. The reactions were quenched on ice and protease inhibitors were added to give a final concentration of 100 μM each of leupeptin, antipain, and soybean trypsin inhibitor. Positive and negative control sperm heads (prepared by the Core Protocol and subsequently either unheated or inactivated at 48° C.) were resuspended in a cocktail of 100 μM protease inhibitors plus 100 μg/ml trypsin.

Example 6
Inactivation of Oocyte Activation Activity of Demembranated Sperm

Spermatozoa were decapitated/demembranated according to the method presented in the Core Protocol. The resulting sperm heads were incubated for 30 minutes in NIM containing various concentrations of the reducing agents DTT or GSH at temperatures of about 0° C. to about 100° C., as illustrated in FIG. 2 and Table 5. The oocyte activation activity (or lack thereof) was measured by the percentage of live oocytes activated, compared to the total number of oocytes surviving injection. An oocyte was considered to be activated if it exhibited both a male and a female pronucleus (2PN) and a second polar body (Pb$_2$).

For total inactivation, the demembranated sperm heads were incubated at 100° C. for 10 minutes or for 46° C. or 49° C. for 30 minutes. In particular, spermatozoa incubated at 44° C. for 30 minutes or 100° C. for 10 minutes were used for several experiments. After incubation, the spermatozoa were pelleted at 2° C. for 50 to 80 minutes at 20,000×g followed by resuspension in fresh media. Complete inactivation of these sperm heads was confirmed by injection of a sample of the heads resuspended in control buffer alone.) The inactivated demembranated heads were then available for injection into mature unfertilized oocytes, as described further below.

Example 7
Collection of Mouse Sperm Cytosolic Extracts

Golden hamster sperm cytosolic extracts were prepared essentially as described previously [K. Swann, Development 110, 1295–1302 (1990)]. For the isolation of mouse sperm cytosolic extracts, caudae epididymides from 4 freshly killed, 12- to 20-week-old B6D2F1 males were finely chopped in CZB-H medium, and the sperm were allowed to disperse before the suspension was filtered through a Kim Wipe. Sperm were then pelleted at room temperature for 5 minutes at 2000×g and resuspended to a density of approximately 3×10$^8$ sperm/ml in NIM μl mM DTT, 100 μM leupeptin, 100 μM antipain, and 100 μg/ml soybean trypsin inhibitor. The suspension was subjected to 4 cycles of freezing (5 minutes per cycle in liquid N$_2$) and thawing (5 minutes per cycle at 15° C.) after which sperm were pelleted at 2° C. for 50 minutes at 20,000×g. The resultant supernatant was carefully removed and prepared for microinjection by the addition of PVP solution (as described in the Core Protocol) and was used within 2 hours of preparation.

Example 8
Microinjection of Oocytes

Microinjection of demembranated sperm heads and sperm-derived material was achieved by piezo-electric microinjection, employing the Piezo Micromanipulator Model MB-U by Prime Tech Ltd. (Tsukuba, Ibaraki-ken, Japan) [Y. Kimura and R. Yanagimachi, Biol. Reprod. 52, 709–720 (1995)]. This unit uses the piezo-electric effect to advance the pipette holder a very short distance (e.g., 0.5 μm) at a time at very high speed. The intensity and speed of the pulse were regulated by the controller. Injections were usually completed within 18 to 19 hours post-hCG administration. Each injection session included positive and negative sperm head controls (with respective average values of 6.4 and 5.4 eggs successfully injected per experiment) and was performed with a single needle to control against single interneedle variation. Data from injection sessions in which positive and negative controls did not respectively give 100% and 0% activation were discarded. (In these experiments overall, 1.2% of positive control injections failed to activate, and 1.4% of negative control injections activated; data not shown.)

For injection into the oocyte, the sample was aspirated into an injection pipette (the injection pipette tip diameter was typically 5 μm) which had been attached to the Piezo electric pipette driving unit. The intensity and speed (frequency) of the pulses were regulated by the controller PMAS-CT01 (controller setting scales: intensity 2, speed 1).

The test solution (usually with a single sperm head) was drawn into the pipette after expulsion of a small amount of mercury into the test solution droplet. This ensured that ahead of the mercury boundary, the test solution filled the pipette and was therefore not diluted further. Since the mercury front typically advanced by about 55 μm (the equivalent of seven mouse sperm head lengths) during injection, the equivalent of approximately 0.5 pl of the test incubation was delivered into the ooplasm when allowance is made for 1:1 dilution in the PVP solution; 0.5 pl corresponds to 0.01 to 0.05 mouse sperm heads in the test incubation according to the Core Protocol.

Mature unfertilized oocytes were positioned on a microscope stage in CZB-H medium. The oocyte was held by a holding pipette and the tip of the injection pipette was brought into intimate contact with the zona pellucida at the 3 o'clock position. Several piezo-pulses (intensity 1–2, speed 1–2) were given to advance the pipette while a light negative pressure was applied to it. When the tip of the pipette had passed through the zona pellucida, a cylindrical piece of zona pellucida in the pipette was expelled into the perivitelline space. After the head of the spermatozoa was pushed forward until its tip almost reached the opposite side of the oocyte's cortex. The oolemma was punctured by applying 1 or 2 Piezo pulses (intensity 1–2, speed 1) and the head of the spermatozoon was expelled into the ooplasm. The pipette was gently withdrawn, leaving the head of the spermatozoon within the ooplasm. All injections were performed in CZB-H at room temperature. Sperm-injected oocytes were maintained in operation medium (CZB-H) for 2 to 60 minutes prior to transfer to CZB under mineral oil equilibrated in 5% (v:v in air) $CO_2$ at 37° C.

Example 9
Artificial Activation of Oocytes

In some experiments, where appropriate, oocytes were artificially activated by incubation, immediately after injection, for 45 to 60 minutes in $Ca^{2+}$-free CZB medium containing 6.7 mM $SrCl_2$ under mineral oil equilibrated in 5% (v:v in air) $CO_2$ at 37° C. [D.G. Whittingham and G. Siracusa, *Exp. Cell Res.* 113, 311–317 (1978); and D. Kline and J. T. Kline, *Dev Biol* 149, 80–89 (1992)]. Eggs were then briefly washed in, and transferred to, fresh CZB medium, and incubation was continued.

Example 10
Manipulation of Embryos and Embryo Transfer

Following oocyte activation, embryos were cultured in vitro in CZB medium for up to 4 days. Two cell embryos (after approximately 1 day of culture) or morulae/blastocysts (after 2.5 to 3.5 days of culture) were transferred to the oviducts of pregnant albino Swiss Webster or pseudopregnant albino ICR/CD1 mice that had been mated with vasectomized males of the same strain on the evening of microinjection [Y. Kimura and R. Yanagimachi, *Biol. Reprod.* 52, 709–720 (1995)]. Young born as a result of in vitro manipulation were thus characterized by their black eyes and coat color.

Figure 3:
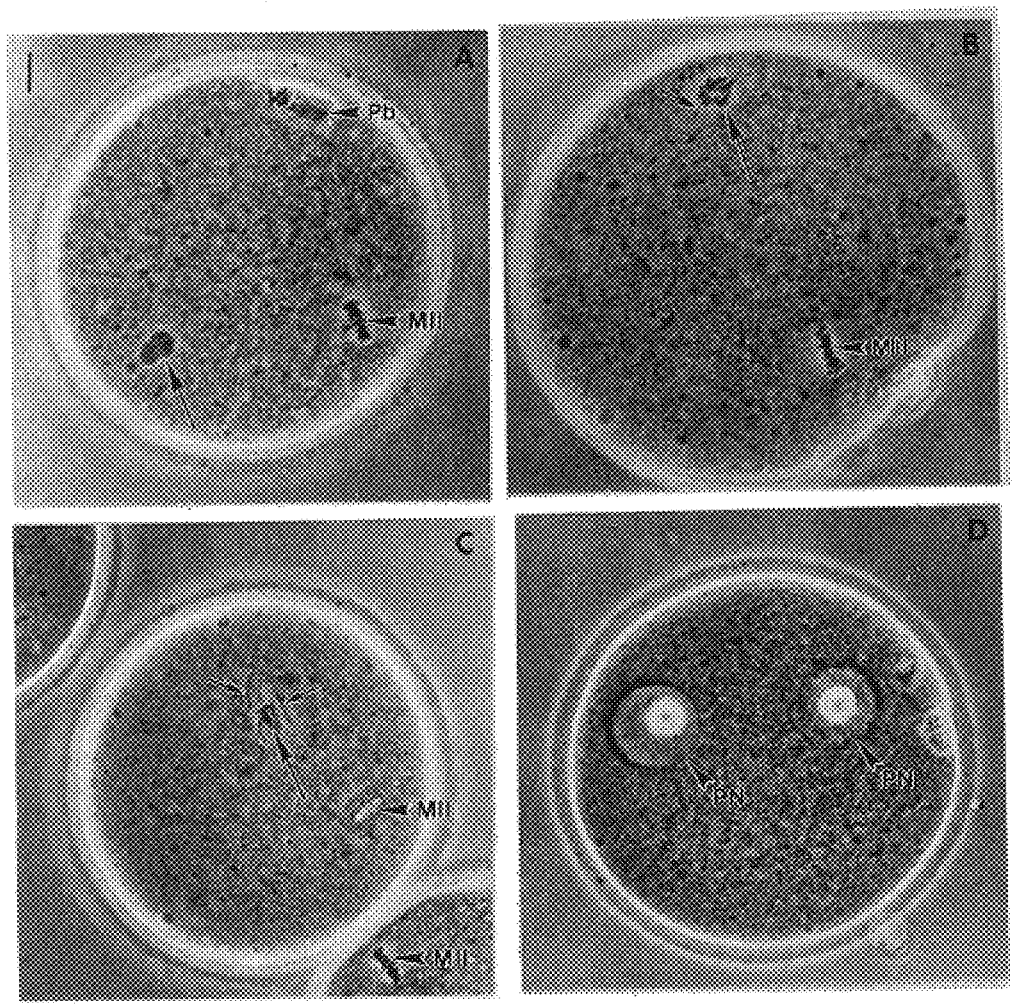
FIG. 3(A–D) is a photomicrograph illustrating aceto-orcein staining of 45° C.-inactivated sperm heads injected into metaphase II oocytes. Oocytes were stained 2 hours (A), 4 hours (B), or 6 hours (C) after the injection of inactivated heads in buffer alone, and zygotes were stained 6 hours after injection of inactivated heads in SOAF, solution (D). Large arrows indicate the male-derived chromatin mass in each oocyte (A–C), with small arrows showing elongated, male-derived chromosomes increasingly apparent after 4 to 6 hours (B and C). Bar=12 µm; MII, female metaphase II chromosomes; Pb, first polar body; PN, pronuclei.

Example 11
Determination of Oocyte Activation and Statistical Processing of Data Ova were scored at 6 to 10 hours postinjection. Eggs that were discernibly dead were counted and discarded. The remainder were examined by light microscopy and/or aceto-orcein staining for activation evidenced by 1) the formation of two clear pronuclei (2PN) (or one in cases in which no sperm head had been injected), 2) the presence of the second polar body ($Pb_2$), and 3) a change to grainy, heterogeneous cytoplasmic texture [Y. Kimura and R. Yanagimachi, *Biol. Reprod.* 52, 709–720 (1995)]. Intra-ooplasmic sperm chromatin de- and recondensation were monitored following aceto-orcein staining of injected metaphase II oocytes. Aceto-orcein staining of 45° C.-inactivated sperm heads injected into metaphase II oocytes is illustrated in FIG. 3. Oocytes were stained 2 hours (A), 4 hours (B), or 6 hours (C) after the injection of inactivated heads in buffer alone, and zygotes were stained 6 hours after injection of inactivated heads in $SOAF_s$ solution (D). In the Figure, large arrows indicate the male-derived chromatin mass in each oocyte (A–C), with small arrows showing elongated, male-derived chromosomes increasingly apparent after 4 to 6 hours (B and C). The first polar body (Pb) is evident in the metaphase II oocyte illustrated in (A).

After sperm head injection, zygotes containing an odd number of pronuclei (number of pronuclei 2 in 6.5% of cases) were scored as having activated. The data in Table 5 illustrate a generally good fit (residual deviance<0.5, 3–5 degrees of freedom) to a logistic-binomial model [D. Brown and P. Rothery in Models in Biology: Mathematics, Statistics, and Computing, Oxford, Clarendon Press, p. 130–135 (1993)], with the exception of those for 15 mM DTT (estimate of regression coefficient=10.1, SE=1.49).

Egg Activation by Demembranated Spermatozoa was Sensitive to Temperature and Reducing Environment The effect of temperature and redox potential on the ability of demembranated sperm heads to activate oocytes is illustrated in FIG. 2 and Table 5. Mouse spermatozoa prepared using the Core Protocol were resuspended in NIM containing 0, 15, or 170 mM DTT (pH 7.07–7.45) or 10 mM GSH and incubated for 30 minutes over a range of temperatures prior to injection into metaphase II oocytes. As illustrated, there is an inverse correlation between temperature and the ability of sperm heads to activate within the range 15° C. to 44° C. Given that the ooplasm of metaphase II mouse oocytes represents a relatively strong intracellular reducing environment [H. I. Calvin, et al., *Gamete Res* 14, 265–275 (1986)], we reasoned that the inclusion of reducing equivalents might also effect the ability of heads to activate, and we tested this over a range of temperatures. We found that the temperature relationship was indeed apparently altered by the inclusion of the reducing agent DTT, with 15 mM DTT rendering sperm more sensitive to temperature and 170 mM DTT rendering them less so below 44° C. Physiological concentrations of the weaker reducing agent, GSH (10 mM; the concentration of GSH within unfertilized metaphase II mouse oocytes is 9 to 10 mM [H. I. Calvin, et al., *Gamete Res* 14, 265–275 (1986)]), rendered sperm heads more acutely sensitive to inactivation at 37° C. but otherwise mirrored results obtained with NIM alone.

In all experiments, the ability of demembranated sperm heads to activate was completely abolished after treatment at or above approximately 44° C. Simultaneous injection of three 47.5° C.-inactivated demembranated heads into each egg also failed to induce activation (data not shown). We investigated the fate within the metaphase II ooplasm of sperm nuclei that had been heated to 45° C. (FIG. 3) or that had been subjected to 100° C. for 10 minutes (data not shown). We found that in both cases, sperm heads had undergone decondensation and were (partially) recondensed into chromosomes within the inactivated, metaphase II oocyte. Sperm heated at 45° C. had initiated the process within 2 hours of injection (FIG. 3(A)), with the formation of chromosomes discernible after 4 hours (FIG. 3(B)) and apparently complete within 6 hours (FIG. 3(C)). This demonstrates that mouse sperm decondensation (in the absence of pharmacological agents) is independent of oocyte activation. In addition, it shows that sperm either do not contribute a factor that is obligate for chromatin decondensation or that the factor is extremely heat stable (and thus unlikely to be enzymatic).

Figure 4:
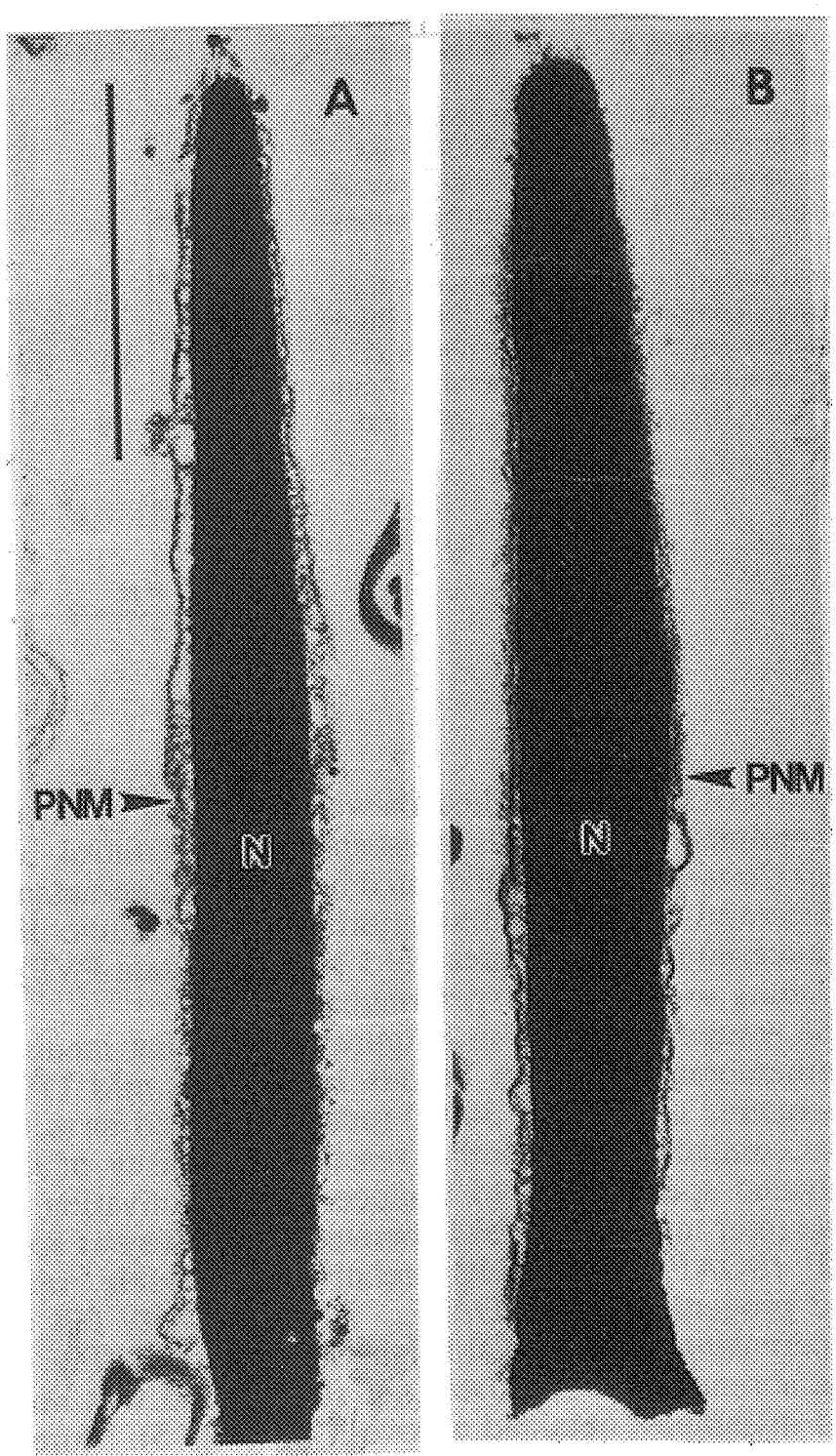
FIG. 4(A–B) is a photomicrograph showing sagittal sections through the heads of mouse spermatozoa that had been subjected to the Core Protocol followed by incubation for 30 minutes in NIM-15 mM DTT at 27° C. (A) or 30 minutes in NIM at 45° C. (B). Bar=1 µm; N, Nucleus; PNM, perinuclear matrix.

As illustrated in FIG. 4, heads that retained much of their ability to activate oocytes (after incubation in NIM-15 mM DTT at 27° C.) were indistinguishable by electron microscopy from those completely lacking activity (after incubation in NIM at 45° C.). From this and our previous work, we infer that some or all of the oocyte-activating function of spermatozoa resides in the perinuclear matrix and is resistant to treatment with Triton X-100 [S. Kuretake, et al., *Biol. Reprod.* 55, 789–795 (1996); and Y. Kimura, et al., *Biol. Reprod.* 58, 1407–1415 (1998)]. Moreover, temperature-induced changes in the ability of sperm heads to activate are thus not due to gross structural alterations of the perinuclear matrix.

It is not possible from these experiments to determine whether the augmented abrogation of sperm-head activating function by 15 mM DTT is a direct, negative (by inhibition of the factor[s] responsible) or an indirect, positive one (stimulating one or more components that subsequently inhibit or remove the activating function). However, the preservation of activating ability by 170 mM DTT (up to about 37° C.) indicates the latter, since it is unlikely that relatively low, but not high, concentrations of DTT would directly abolish the activating function. This would be consistent with either the destruction of sperm-borne activating factor(s) or the liberation of SOAF from the sperm head in an active form. To investigate this further, we determined whether SOAF activity could be demonstrated in the supernatant after incubation of membrane-free sperm heads in NIM-15 mM DTT.

Temperature-sensitive Loss of Sperm-activating Function was Efficiently Rescued by Trans-complementing, Solubilized SOAF Derived from Insoluble Sperm Compartments Supernatant generated by incubation of membrane-free sperm heads in NIM-15 mM DTT over a range of temperatures was used to resuspend cells whose activity had been abolished by parallel treatment at either 100° C. for 10 minutes or 46° C. to 49° C. for 30 minutes. (In each experiment, complete inactivation of these sperm heads was confirmed by injection of a sample of the heads resuspended in control buffer alone). Coinjection of inactivated heads and supernatant enabled careful control and monitoring of the volume of soluble material injected (typically 1 pl [supernatant-PVP] corresponding to 0.01 to 0.05 spermatozoa).

The results presented in FIG. 5 show that incubation of demembranated sperm heads in NIM-15 mM DTT at temperatures of 27° C. or 30° C. indeed liberated an activity whose coinjection efficiently rescued the ability of 48° C.-inactivated spermatozoa to induce oocyte activation. We refer to the factor(s) liberated in this way as soluble SOAF (SOAF$_s$) and to its relatively insoluble, matrix bound progenitor(s) as SOAF$_m$. SOAF$_s$ activity fell away in supernatants generated at higher temperatures or in the absence of DTT (data not shown) and was not detected in samples obtained above 37° C. Moreover, heating SOAF$_s$ at 48° C. abolished its activity in a manner that mimicked heat inactivation of whole heads (Table 1). This finding, the observation that SOAF$_s$ is liberated at temperatures at which sperm heads start to lose their activity, and the apparent origin of SOAF$_s$ from a compartment known to enter the egg at fertilization, strongly suggest that SOAF$_s$ is involved in oocyte activation and is responsible for the observed temperature sensitivity of spermatozoa in this respect.

When heads that had been incubated at 37° C. in NIM-1 5mM DTT were injected, only 3.8% of eggs were activated (FIG. 2). This is consistent with loss of activity from heads due to liberation of insoluble, matrix SOAF (SOAF$_m$) into the surrounding medium in a soluble form (the SOAF$_m$→SOAF$_s$ transition). However, SOAF activity was also not high in the resulting supernatant, with trans-complementation of inactivated heads in only 2 of 17 (11.8%) of injections (FIG. 5). We wished to investigate whether the absence of activity in the supernatant generated at 37° C. reflected an inherent SOAF$_s$ instability at this temperature. We found that SOAF$_s$ activity generated at 27° C. survived incubation for a further 30 minutes at 37° C., giving 100% activation when coinjected with inactivated sperm heads (Table 1). This finding, coupled with the inability of supernatants generated at 37° C., but not 27° C., to promote efficient activation, indicates SOAF$_s$ degradation in the presence but not absence of sperm heads (Table 1; FIG. 5). As part of our ongoing investigation of this phenomenon, we sought to reproduce the degradation of SOAF$_s$ generated at 27° C. by trypsin proteolysis. We found that SOAF$_s$ activity was indeed abolished after treatment with trypsin (Table 1). The sensitivity of SOAF$_s$ to trypsin and heat suggests that it is proteinaceous.

The loss of activation function in 48° C.-heated mouse sperm could be efficiently rescued in SOAF$_s$ samples generated by incubation of demembranated sperm from the human, pig, bull, or hamster in NIM-15 mM DTT at 27° C. (data not shown). SOAF$_s$ is therefore not highly species specific. Demonstration of SOAF$_s$ has been achieved using pig sperm heads that have been highly purified, with <5% contamination by tail fragments (data not shown). Porcine SOAF$_s$ activity resides in extracts that are typically 200 to 400 μg total protein/ml (that is, a maximum of approximately 6 pg of soluble, sperm-derived protein is introduced per injection). Furthermore, SOAF$_s$ from the pig and mouse activated mouse oocytes sufficiently for embryonic development to the blastocyst stage and beyond, to term (Table 2). Developmental rates (to term) of oocytes activated by SOAF$_s$ or treatment with SrCl$_2$ are similar, but low. However, analysis of oocytes injected with sperm prepared according to the Core Protocol revealed a very high level of structural abnormalities in male-derived chromosomes (data not shown). These data suggest that the low developmental rate reflects chromosomal damage resulting from sperm preparation using the Core Protocol.

Lack of Evidence for a Direct Interaction Between 48° C.-heated Demembranated Spermatozoa Heads and SOAF$_s$ in Initiating Activation To probe further the nature of any interaction between coinjected SOAF$_s$ and inactivated sperm heads, we injected SOAF$_s$ alone or with latex beads as adjuvants (i.e., in the absence of heads). Neither treatment induced the resumption of meiosis (Table 3). However, SOAF$_s$ was capable of rescuing heat-inactivated spermatozoa that had previously been sonicated either not at all or briefly in the absence of Triton X-100 (data not shown). In this situation, sites that would have been exposed for specific SOAF$_s$ binding in Triton X-100-demembranated cells presumably remain largely occluded. If so, any SOAF$_s$ complexes forming on these cells would presumably be nonspecific or form intraooplasmically.

The potential for interaction between SOAF$_s$ and inactivated heads was probed further by injecting SOAF$_s$ and inactivated heads into the same egg but at separate times. Oocytes were first injected with inactivated heads (in NIM-15 mM DTT) and then subsequently injected with SOAF$_s$ after incubation at 37° C. for either 2 hours or 4 hours. This resulted in activation of 11 of 14 (79%) of oocytes although negative controls in which the secondary injection was with SOAF$_s$ that had been inactivated by heating at 48° C. for 30 minutes failed to activate (0 of 5). This shows that SOAF$_s$ possesses activity in the absence of inactivated heads (i.e., they do not merely stabilize SOAF$_s$) and that exposure of the ooplasm to heads and SOAF$_s$ does not have to be simultaneous for activation to occur. Given the rapid excoriation of the sperm head within the ooplasm [R. Yanagimachi and Y. D. Noda, Am. J. Anat. 128, 429–462 (1970); and N. Usui, Mol. Reprod. Dev. 44, 132–140 (1996) (FIG. 3A) this strongly suggests that SOAF$_s$ does not potentiate activation by modifying heads.

Further Characterization of Detergent-resistant SOAF Reveals Additional Properties Distinct from Those of Cytosolic Oocyte-activating Function The identification of an egg-activating finction that is detergent resistant (SOAF) strongly suggests that it is distinct from the cytosolic sperm factors whose prototype is glucosamine 6-phosphate isomerase-oscillin [J. Parrington, et al., Nature 379, 364–368 (1996)]. We adopted two approaches to compare SOAF and cytosolic sperm factors from a single species. First, we applied the Core Protocol to golden hamster sperm and then performed incubation at 27° C. in NIM-15 DTT. This preparation was capable of trans-complementing heat-inactivated mouse sperm heads sufficient for activation of 100% (5 of 5) of surviving oocytes injected. A freeze-thaw protocol originally utilized in the isolation of the cytosolic, $Ca^{2+}$-mobilizing activity from hamster [K. Swann, Development 110, 1295–1302 (1990); and G. D. Palermo, Mol. Hum. Reprod. 3, 367–374 (1997)] liberated a hamster cytosolic activity that readily activated 100% of mouse eggs when injected alone (Table 4) This is consistent with the coexistence of SOAF and glucosamine 6-phosphate isomerase-oscillin in hamster sperm. Second, we adapted the protocol to the isolation of mouse sperm cytosolic factors. Using this method, we found that the mouse sperm indeed possessed a soluble, cytoplasmic function that activated approximately 40% of oocytes when injected alone (Table 4). This level is possibly less than 100% due to a combination of 1) relatively low sperm density ($3 \times 10^8$ sperm/ml compared to about $10^9$ sperm/ml for hamster); 2) the comparatively small size of mouse sperm head soluble compartments, particularly the principal segment of the acrosome; and 3) the liability of the activity at 25° C. In one experiment, activity dropped from 50% (7 of 14 activated) after approximately 50 minutes to 10% (1 of 10 activated) after approximately 100 minutes. In contrast, SOAF$_s$ activity is stable at 25° C. for at least several hours (data not shown). Cytosolic activity was also readily demonstrable by coinjection of the soluble fraction either with sperm fragments that had been subjected to 48° C. for 30 minutes or with amine-modified latex beads (Table 4). In marked contrast to the freeze-thaw generated, cytosolic fraction, injection of SOAF$_s$ in the absence of sperm heads consistently failed to activate (Table 3). This failure was exhibited even when SOAF$_s$ was isolated from the relatively high density of greater than $5 \times 10^8$ porcine sperm/ml and injected immediately after preparation; 0% (0 of 6) of oocytes became activated when this SOAF$_s$ was injected alone, but 100% (5 of 5) became activated when injected in the presence of inactivated mouse sperm heads.

In all cases, mouse sperm heads subjected to the freeze-thaw disruption of cytoplasmic compartments were subsequently capable of oocyte activation, even after they had been subjected to Triton X-100 extraction in the Core Protocol (Table 4). Hence, sperm heads subjected to freeze-thawing retained the ability to initiate activation via native matrix and other components. Moreover, 5 of 5 oocytes were activated by the injection of heads prepared by the Core Protocol with 5 mg/ml BSA included throughout (to minimize "stickiness" of the heads). Continued inclusion of 5 mg/ml BSA had no discernible effect on the generation of SOAF$_s$ (in NIM-DTT at 30° C.), which activated 100% (9 of 9) of oocytes when injected with 48° C.-treated sperm heads. Demembranated sperm heads are therefore not merely an adhesive vehicle for cytosolic, sperm-derived factors such as glucosamine 6-phosphate isomerase-oscillin.

While the invention has been described herein with reference to the preferred embodiments, it is to be understood that it is not intended to limit the invention to the specific forms disclosed. On the contrary, it is intended to cover all of the manifold modifications and alternative forms falling within the spirit and scope of the invention.

TABLE 1

Characterization of Heat and Trypsin Sensitivity of SOAF$_s$ with Respect to Oocyte Activation

| Sample Treatment[a] | No. (%) oocytes | | |
|---|---|---|---|
| | Injected | Survived | Activated |
| SOAF$_s$ + heat | | | |
| 27° C., 45 min | 9 | 9 | 9 (100) |
| 37° C., 30 min | 18 | 15 | 15 (100) |
| 48° C., 10 min | 12 | 12 | 0 (0) |
| 48° C., 30 min | 11 | 9 | 0 (0) |
| SOAF$_s$ + trypsin | | | |
| 50 µg/ml | 25 | 21 | 3 (14) |
| 100 µg/ml | 24 | 21 | 0 (0) |

[a]SOAFs samples were prepared following incubation of spermatozoa prepared by the Core Protocol in NIM-15 mM DTT for 30 min at 27° C. Heads in 15 mM DTT-NIM heated to 48° C. for 10 min failed to induce activation (0/6).

TABLE 2

In Vitro Culture and Transfer or Embryos Generated by the Injection of Heat-Inactivated, Demembranated Sperm Heads Whose Activating Function was Rescued by SOAF$_s$ or $Sr^{2+}$

| | No. Oocytes | | No. Oocytes Developed to[b] | | No. |
|---|---|---|---|---|---|
| Agent[a] | Survived | Activated (%) | 2-8-Cell | Mor/Blast[c] | Offspring (sex) |
| None | 116 | 0 (0) | — | — | — |
| $Sr^{2+}$ | 66 | 66 (100) | 25 | <u>40</u> | 0 |
| | 67 | 67 (100) | <u>63</u> | — | 4 (2M, 2F)[d] |
| musSOAF$_s$[c] | 34 | 34 (100) | 11 | <u>9</u> | 0 |
| | 45 | 45 (100) | <u>36</u> | — | 1 (M)[e] |
| porSOAF$_s$[c] | 126 | 96 (76) | 18 | <u>19</u> | 2 (M, F) |
| | 88 | 41 (47) | <u>36</u> | — | 2 (M, F)[d] |

[a]Each experiment included confirmation that sperm heads had been effectively heat inactivated by injection of those heads alone (grouped in the top row, labeled 'None') with an average of 11.6 per experiment. SOAF$_s$ samples were generated following incubation of spermatozoa prepared by the Core Protocol in NIM-15 mM DTT for 30 min at 27° C.
[b]Underlined numbers denote the developmental stage at which embryos were transferred.
[c]mor/blast, morulla/blastocyst; mus, mouse; por, pig.
[d]Littermates developed apparently normally to adulthood and were crossed with nonexperimental animals to produce live young.
[e]Stillborn.

TABLE 3

The Ability of SOAF$_s$ to Elicit Oocyte Activation in the Presence of Absence of Heat-Inactivated Sperm Heads

| Injection of | | | No. (%) Oocytes | | |
|---|---|---|---|---|---|
| Head | Bead[a] | SOAF$_s$[b] | Injected | Survived | Activated |
| + | --- | + | 34 | 30 | 30 (100) |
| --- | --- | + | 46 | 45 | 0 (0) |
| --- | + | + | 20 | 20 | 0 (0) |

[a]Injections included 3–5 beads per oocyte.
[b]Preparation of SOAF$_s$ was as per Table 2.

TABLE 4

The Ability of Freeze-Thaw-Derived Sperm Material to Elicit Oocyte Activation

| SAMPLE[a] | | | | | No. (%) Oocytes | | |
|---|---|---|---|---|---|---|---|
| Cyt | Beads | Heads | CP-Heads | Fragments | Injected | Survived | Activated |
| + | -- | -- | -- | -- | 58 | 56 | 21 (38) |
| + | -- | -- | -- | + | 33 | 18 | 17 (94) |
| + | + | -- | -- | -- | 10 | 10 | 3 (30) |
| -- | -- | + | -- | -- | 18 | 18 | 18 (100) |
| -- | -- | -- | + | -- | 15 | 15 | 15 (100) |
| +[b] | -- | -- | -- | -- | 33 | 11 | 11 (100) |

[a]Sperm were subjected to cycles of freezing and thawing to liberate soluble material (cytosol) as described in "Example" section. All material was from sperm that had been subjected to cycles of freeze-thawing, except 48° C.-heated sperm fragments (heads and tails), which were prepared by the Core Protocol alone. Column headings are: Cyt, cytosolic fraction; Beads, amine-modified latex beads; heads, heads following freeze-thaw cycles; CP-Heads, Heads subjected to freeze-thaw cycles and subsequently to the Core Protocol; Fragments, 48° C.-heated head and tail fragments.
[b]Cytosolic fraction derived from hamster sperm; all other material was from the mouse.

TABLE 5

Number of Oocytes Successfully Injected (Number of Injected Oocytes Activated)

| Temperature | 0° C. | 15° C. | 21° C. | 27° C. | 30° C. | 33.5° C. | 36–37° C. | 36.5° C. | 43.5° C. | 45–50° C. | 100° C. |
|---|---|---|---|---|---|---|---|---|---|---|---|
| 0 mM DTT ⊙ | 38 (38) | — | — | — | 27 (26) | 29 (22) | 29 (11) | — | 24 (0) | 5 (0) | 37 (0) |
| 10 mM GSH ■ | 15 (15) | — | — | 14 (14) | — | 10 (7) | 8 (0) | — | — | 19 (0) | — |
| 15 mM DTT □ | 70 (70) | 19 (19) | 29 (28) | 18 (12) | 18 (4) | — | 26 (1) | 32 (1) | 13 (0) | 44 (0) | 49 (0) |
| 170 mM DTT △ | 53 (53) | — | — | — | — | — | 7 (7) | 49 (34) | 13 (0) | 13 (0) | 30 (0) |

We claim:

1. A method of in vitro activation of oocytes, comprising the steps of:
   (a) providing an unfertilized mammalian oocyte comprising ooplasm;
   (b) providing mature mammalian spermatozoa of the same species as the oocyte;
   (c) treating the spermatozoa with a detergent under non-denaturing conditions that provide demembranated spermatozoa heads comprising nuclei and matrix-bound perinuclear material that retain oocyte activation activity when injected into the ooplasm of oocytes;
   (d) incubating a first aliquot of the demembranated spermatozoa heads in a physiological medium containing a reducing agent at about 0° C. to about 37° C.;
   (e) obtaining a supernatant from the incubated first aliquot;
   (f) incubating a second aliquot of the demembranated spermatozoa heads in a physiological medium at a temperature of about 44° C. for about 30 minutes to about 100° C. for about 10 minutes, to abolish oocyte activation activity;
   (g) inserting an inactivated demembranated spermatozoon head from step (f) into the ooplasm of the oocyte; and
   (h) inserting a portion of the supernatant from step (e) into the ooplasm of the oocyte, wherein the insertion of the inactivated demembranated spermatozoon head and the portion of the supernatant result in activation of the oocyte.

2. The method of claim 1, wherein the insertion steps (g) and (h) are combined and comprise the substep of suspending the inactivated demembranated spermatozoa heads from the second aliquot in the supernatant from the first aliquot, and the insertion step comprises inserting a portion of the suspension containing the supernatant and an inactivated demembranated spermatozoon head into the ooplasm of the oocyte.

3. The method of claim 1, wherein the treating step (c) comprises the substep of sonicating the spermatozoa to separate the spermatozoa heads from tails.

4. The method of claim 1, wherein the reducing agent in the physiological medium for incubating the first aliquot of demembranated spermatozoa heads is selected from the group consisting of dithiothreitol and reduced glutathione.

5. The method of claim 4, wherein the dithiothreitol is present in the medium at about 15 millimolar.

6. The method of claim 4, wherein the reduced glutathione is present in the medium at about 10 millimolar.

7. The method of claim 1, wherein the first aliquot of the demembranated spermatozoa heads is incubated at about 15° C. to about 34° C.

8. The method of claim 7, wherein the first aliquot of the demembranated spermatozoa heads is incubated at about 27° C. to about 30° C.

9. The method of claim 1, wherein the first aliquot is incubated for about 30 minutes.

10. The method of claim 1, wherein the physiological medium for incubating the second aliquot of the demembranated spermatozoa heads further comprises a reducing agent.

11. The method of claim 10, wherein the reducing agent is selected from the group consisting of dithiothreitol and reduced glutathione.

12. The method of claim 11, wherein the dithiothreitol is present in the medium at about 15 millimolar to about 170 millimolar.

13. The method of claim 11, wherein the reduced glutathione is present in the medium at about 10 millimolar.

14. The method of claim 1, wherein the second aliquot is incubated at about 44° C. to about 48° C. for about 30 minutes.

15. The method of claim 1, wherein the mammalian oocyte is obtained from a mammal selected from the group consisting of mouse, rabbit, hamster, human, cow and pig.

16. The method of claim 15, wherein the oocyte is obtained from a mouse.

17. The method of claim 1, wherein the mammalian spermatozoa are obtained from a mammal selected from the group consisting of mouse, rabbit, hamster, human, bull and boar.

18. The method of claim 15, wherein the supernatant is obtained by incubation of demembranated sperm from a mammal selected from the group consisting of human, pig, bull, rabbit, mouse and hamster, and the inactivated demembranated spermatozoa heads and the oocyte are obtained from a different mammalian species selected from the group consisting of human, pig, bull, rabbit, mouse and hamster.

19. The method of claim 15, wherein the supernatant is obtained by incubation of demembranated sperm from a mammal selected from the group consisting of human, pig, bull, mouse and hamster and the inactivated demembranated spermatozoa heads and the oocyte are obtained from a mouse.

20. A method of in vitro activation of oocytes, comprising the steps of:

(a) providing an unfertilized mammalian oocyte comprising ooplasm;

(b) providing mature mammalian spermatozoa from at least a first and a second mammalian species, wherein at least one of the mammalian species is the same species as that of the mammalian oocyte;

(c) treating the spermatozoa from the at least first and second mammalian species with a detergent under non-denaturing conditions that provide demembranated spermatozoa heads comprising nuclei and matrix-bound perinuclear material that retain oocyte activation activity when injected into the ooplasm of oocytes;

(d) incubating a first aliquot of the demembranated spermatozoa heads from the at least first or second mammalian species in a physiological medium containing a reducing agent at about 0° C. to about 37° C.;

(e) obtaining a supernatant from the incubated first aliquot;

(f) incubating a second aliquot of the demembranated spermatozoa heads from the mammalian species that is the same species as the mammalian oocyte in a physiological medium at a temperature of about 44° C. for about 30 minutes to about 100° C. for about 10 minutes, to abolish oocyte activation activity;

(g) inserting an inactivated demembranated spermatozoon head from step (f) into the ooplasm of the oocyte; and (h) inserting a portion of the supernatant from step (e) into the ooplasm of the oocyte, wherein the insertion of the inactivated demembranated spermatozoon head and the portion of the supernatant result in activation of the oocyte.

* * * * *